United States Patent [19]

Orr et al.

[11] Patent Number: 4,835,098
[45] Date of Patent: May 30, 1989

[54] CHARACTERIZATION OF HLA ALLELES WITH LOCUS-SPECIFIC DNA PROBES

[75] Inventors: Harry T. Orr; Beverly H. Koller, both of Minneapolis, Minn.

[73] Assignee: Regents of University of Minnesota, Minneapolis, Minn.

[21] Appl. No.: 772,561

[22] Filed: Sep. 4, 1985

[51] Int. Cl.[4] .................... C12Q 1/68; C07H 15/12
[52] U.S. Cl. .................... 435/6; 435/172.3; 436/63; 436/501; 436/808; 536/27; 935/12; 935/29; 935/78
[58] Field of Search ............ 435/6, 172.3; 436/63, 436/501, 808; 536/27; 935/12, 29, 78

[56] References Cited

U.S. PATENT DOCUMENTS 4,394,443  4/1983  Weissman et al. .................... 435/6

FOREIGN PATENT DOCUMENTS 0070687  1/1983  European Pat. Off. .

OTHER PUBLICATIONS

Cohen, D., et al., "Analysis of HLA class I genes with restriction endonuclease fragments . . . ", Proc. Natl. Acad. Sci. USA 80 6289-6292 (Oct. 1983).
F. C. Grumet et al., Mol. Biol. Med., 1, 501 (1983).
H. L. Ploegh et al., Proc. Natl. Acad. Sci USA, 77, 6081 (1980).
B. H. Koller et al., J. Immunology, 134, 2727 (1985).
J. Vieira et al., Gene, 19, 259 (1982).
H. T. Orr et al., Nature, 302, 534 (1983).
H. T. Orr et al., Immunogenetics, 18, 489 (1983).
B. H. Koller et al., Proc. Natl. Acad. Sci. USA, 81, 5175 (1984).

Primary Examiner—Robert J. Warden
Assistant Examiner—Richard Wagner
Attorney, Agent, or Firm—Merchant, Gould, Smith, Edell, Welter & Schmidt

[57] ABSTRACT

HLA class I and class II locus specific DNA probes are prepared by cloning DNA segments obtained from the 3'-untranslated region and the 5' flanking region of isolated alleles. The probes are useful to determine the HLA alleles present in an individual.

19 Claims, 2 Drawing Sheets

4,835,098

CHARACTERIZATION OF HLA ALLELES WITH LOCUS-SPECIFIC DNA PROBES

This invention was made with Government support under Grant Number AI 18124, awarded by the National Institute of Health. The Government has certain rights in this invention. This invention was also made with support from the Leukemia Society of American and the Searle Foundation.

BACKGROUND OF THE INVENTION

The major histocompatibility complex (MHC) includes the HLS gene complex which is located on the short arm of human chromosome 6, as depicted in FIG. 4. This region encodes cell-surface proteins which regulate the cell-cell interactions of the immune response. The various HLA class I loci encode the HLA antigens, 44,000 dalton polypeptides which associate with 2 microglobulin at the cell surface. These class I molecules are involved in the recognition of target cells by cytotoxic T lymphocytes. HLA class II loci encode cell surface proteins of 29,000 and 34,000 daltons. These class II molecules are also involved in the regulation of the immune response.

The HLA-A and HLA-B loci of the HLA Class I genes exhibit an extremely high degree of polymorphism. The 1984 International Histocompatibility Testing Workshop designated 19 alleles of HLA-A (HLA-A1, A2, etc.) and 36 alleles of HLA-B. See, Human Immunology, 11, 117 (1984). Since this high degree of polymorphism is thought to relate to the function of the HLA-A and HLA-B molecules, much effort has gone into determining its molecular basis. With the recent cloning of certain HLA class I genes this effort has extended to the DNA level.

Currently, serological HLA typing is routinely done in connection with many medical procedures, e.g., organ transplantation. Rejection of organ grafts is believed to be diminished if the HLA alleles of donor and recipient are identical. The numerous alleles of HLA genes in the population also make HLA typing useful for paternity testing.

During pregnancy women can develop antibodies to fetal HLA antigens of paternal origin. Sera obtained from these women are qualitative as these sera contain a mixture of antibodies often directed against several HLA alleles. In addition, a considerable effort must be directed towards the ongoing identification of new sera and the determination of their specificity. Monoclonal antibodies to class I antigens have been described. However, only a few uniquely define the alleles according to locus. Furthermore, the genetic complexity of the HLA class I gene family as indicated by hybridization techniques and genomic cloning is much greater than the HLA-A, -B and -C loci which can be serologically defined. For example, Southern blot analysis using a cross-reactive class I cDNA probe suggests that there are 15 to 20 class I genes in the human genome. This complexity has restricted the correlation of polymorphic restriction endonuclease fragments with HLA class I alleles.

One approace to developing locus specific DNA probes from cross-reactive HLA class I genomic clones is disclosed by F. C. Grumet et al., in Mol. Biol. Med., 1, 501 (1983), for the HLA-B locus. The DNA sequences of the B7 gene and a class I pseudogene were compared to locate non-homologous segments. One such segment, including approximately 180 nucleotides comprising the last (7th) intron of the B7 gene was isolated and subcloned to yield a DNA probe reported to be specific for the HLA-B locus.

Therefore a need exists for improved methods to determine the HLA class I allele or alleles expressed by a given individual, e.g. to facilitate tissue matching. One such method can be based on the ability to assign the restriction fragments obtained from the HLA gene complex to individual HLA alleles. A further need exists for methods to map the restriction sites present in individual HLA alleles, particularly those which are polymorphic.

SUMMARY OF THE INVENTION

The present invention is directed to HLA locus specific DNA probes. In contrast to the approach employed by Grumet, et al., these probes can be obtained by cloning DNA segments obtained from highly conserved, or non-variable regions of the HLA gene family. Such regions have been found to include the 3' untranslated region and the 5' flanking region of alleles associated with the HLA class I gene family, such as HLA-2A or HLA-B8. When labelled and denatured, the resultant single-stranded DNA probes hybridize only with DNA derived from alleles present at a common locus. Further, the present probes hybridize with DNA derived from substantially all of the alleles of the locus. In a like manner, locus specific DNA probes can be derived from the HLA class II gene family, e.g. from the HLA-DR, -DQ or -DP loci.

For example, a DNA probe derived from the HLA-A2 allele according to the present invention will hybridize with all of the other HLA-A alleles such as HLA-A2, A3, A11, etc., but will exhibit no significant cross-reactivity with other HLA class I genes, such as the HLA-B alleles. These probes provide a method for the rapid assignment of cloned class I genes to their locus, e.g., to the HLA-A or -B locus. Furthermore, the present probes can be employed to map the recognition sequences for endonucleases relative to the coding regions of the individual alleles of a given locus. for example, the use of two HLA-A specific DNA probes and the techniques of Southern blotting has achieved the placement of the cleavage sites for five endonucleases with respect to the coding region of 15 HLA-A alleles, four of which were found to be associated with unique restriction fragments. This is especially useful for HLA-typing and for examining the basis of disease associations that have been identified for several class I alleles. See F. C. Grumet, HLA Disease Associations, in Clin. Immunol. Rev., 2, 123 (1983). The probes are also useful for studying the expression of the HLA loci at the m-RNA level.

DETAILED DESCRIPTION OF THE INVENTION

Figure 1:
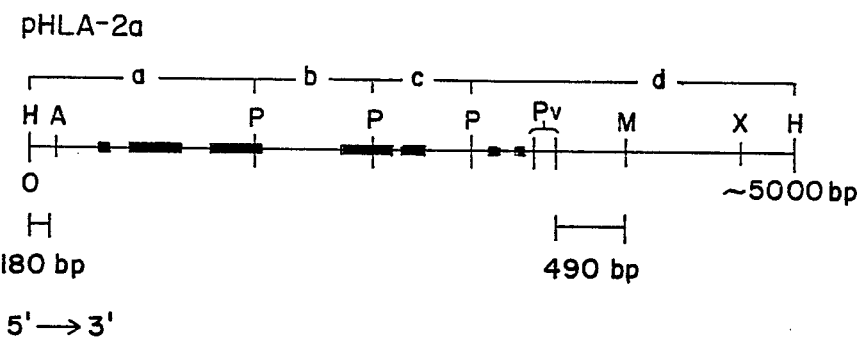
FIG. 1 depicts the localization of the HLA-A specific probes from the 3'-untranslated region and 5' flanking region of the HLA-A2 genomic clone pHLA-2a. The 5' specific probe HLA-2a.2 is the 180bp HindIII-AluI fragment and the 3' probe HLA-2a.1 is the 490bp PvuII-MspI fragment. Restriction endonuclease cut sites indicated are A, AluI; H, HindIII; M, MspI; P, PstI; Pv, PvuII; X, XbaI. Not all of the sites for these enzymes are indicated. The sequence is shown 5' to 3'. Coding regions on the clone are indicated by solid boxes.

DNA gene probes comprise segments of labelled, single-stranded DNA which will hybridize, or noncovalently bond, with complementary single-stranded DNA derived from the gene sought to be identified. The target DNA can readily be derived by the enzymatic fractionation and denaturation of genomic DNA to yield a complex mixture incorporating the DNA from many different genes including the alleles of the HLA loci. A specific DNA gene probe will hybridize only with DNA derived from its target gene or gene fragment, and the resultant complex can be isolated and identified by techniques well known in the art.

DNA probes can be obtained by generating fragments of double-stranded DNA derived from the target genome by digestion with selected restriction endonucleases. The genetic DNA can be derived from a wide variety of cell lines which are identified by their expression of the genes desired to be located. For example, human lymphoblastoid cell lines which express HLA class I antigens have been characterized. Such cell lines include LKT and LCL-721. Loss mutants of LCL 721 can also be employed as sources of genomic DNA in the present invention. Such mutants can be produced by gamma irradiation, followed by selection with complement and alloantisera, or with monoclonal antibodies directed against HLA antigens. Procedures useful for the selection, cloning, karyotyping and phenotypic analysis of such cell lines are well-known in the art. See R. De Mars, et al., Human Immunology, 11, 77 (1984) and the references cited therein.

The genomic DNA isolated from the cell lines is then digested with selected restriction endonucleases to yield fragments containing varying numbers of base pairs (bp). The fragments can be separated according to molecular weight by chromatographic techniques and those determined to correlate with complete class I genes can be ligated into the appropriate DNA vectors. Such vectors include well-characterized plasmid and phage vectors such as plasmid pBR322. The hybrid vectors can be introduced into appropriate host cells, e.g. by the transformation, transdution or transfection of unicellular organisms such as bacteria. Cloned bacteria containing DNA derived from the target class I gene can be identified by techniques such as colony hybridization. Manipulation of the target gene is preferably simplified by subcloning the class I DNA so that a single HLA class I allele is localized along with a relatively small amount of flanking DNA on a small vector such as plasmic pUC9. The HLA DNA segment can then be isolated and sequenced by known techniques [F. Sanger, et al., J. Mol. Biol., 143, 161 (1980)] and its restriction sites mapped. Location of the restriction sites on an HLA allele permits the controlled fragmentation of the allele by restriction endonucleases to yield DNA segments derived from specific regions of a given allele.

To complete the synthesis of the present probes, detectable labels are introduced into sequences of DNA derived from the 3'-untranslated and 5'-flanking region of HLA alleles, e.g. a radiolabel or fluorescent molecule. For example, probes can be made radioactive using the method of nick-translation. Single strand breaks, or "nicks," are introduced at widely separated intervals in double stranded DNA by limited digestion with the enzyme DNase I. At each break, DNA polymerase I of E. coli is used to 1) incorporate radio labeled nucleotides at a free 3'-OH group and 2) extend the nick along the DNA duplex by the 5'→3' exonucleolytic activity of polymerase I. The end result is a double stranded DNA molecule which incorporates radiolabeled nucleotides randomly into each strand.

The strong and specific association between biotin (vitamin H) and the egg-white glycoprotein avidin can provide the basis for a non-radioactive means of detecting DNA:DNA hybridization. The enzymatic incorporation by nick-translation of boitinylated nucleotides into double-stranded DNA has been disclosed. The biotinylated DNA is then used to probe target DNA fragments in a manner similar to the use of radiolabelled probes. Specific DNA:DNA hybridization is then detected by soaking the blot in a solution containing the avidin protein. Avidin binds to the DNA:DNA complexes via the biotin group on the DNA probe. The avidin:biotin:DNA complexes are detected utilizing an indicator enzyme attached to the avidin protein. This enzyme catalyizes the formation of a precipitate which permits the visualization of the DNA:DNA complex as a band of colored material. For example, see U.S. Pat. No. 4,228,237, the disclosure of which is incorporated by reference herein.

A rapid means for synthesizing fluorescent derivatives of oligonucleotides has been developed. This method offers an additional nonradioactive means of detecting specific DNA fragments. For HLA typing, synthetic copies of a portion of each gene specific probe would be synthesized and fluorescently derivatized. Different dye-oligonucleotide conjugates would be synthesized for each HLA gene, HLA-A, HLA-B & HLA-C, each with separate spectral properties. These fluorescent probes would be used in a manner identical to that described for the radioactive probes and hybridization detected by fluorometry. However, a mixture of all three probes could be employed to probe a single DNA fragment mixture, since hybridization of each probe can be visualized by a band of fluorescence at a discrete wavelength.

For use as a probe in DNA:DNA hybridization analysis, the labelled DNA is denatured, i.e. made into single-stranded DNA, as by exposure to elevated temperatures in an aqueous medium.

The resultant single-stranded DNA is brought into contact with denatured DNA fragments derived from the genome sought to be characterized. The labelled probe will hybridize, or bind, only to DNA strands comprising complementary base pair sequences, thus identifying DNA fragments derived from alleles present at a common locus.

A number of experimental techniques have been developed to assay mixtures of genomic DNA fragments with radiolabelled DNA probes. A preferred assay has been disclosed by E. M. Southern, in J. Mol. Biol., 98, 503 (1975). In "Southern blotting," the DNA fragments to be screened are transferred from an agarose gel to a solid support such as a nitrocellose or nylon membrane. The membrane permits the bound DNA to be analyzed by DNA:DNA or DNA:RNA hybridization methods. In a first step, the fragments generated by digestion of genomic DNA by one or more restriction endonucleases are separated chromatographically in an agarose gel by electrophoresis according to their size. The fragments in the gel are treated for 30 minutes at room temperature in aqueous acid, and are then denatured under basic conditions. Finally, the gel is neutralized and placed on top of buffer-saturated filter paper. The ends of the filter paper extend into a resevoir containing the buffer. The top surface of the gel is covered with the membrane onto which the DNA is to be absorbed, or "blotted". The membrane is then overlaid with dry filter paper and a stack of dry absorbent paper towels. A weight is placed on the stack of paper to ensure even contact between the membrane and gel. Buffer carrying the single-stranded DNA is abosrbed by the dry paper as it passes up through the gel. The DNA then binds to the membrane. The blotting procedure usually takes from about 4 to 16 hours to transfer all of the DNA from the gel to the membrane. After transfer, the membrane is heated to firmly attach the DNA to the membrane. Solutions containing radiolabelled probes can then be brought into contact with the genomic DNA fragments fixed to the membrane. Any hybridization is detected by autoradiography, e.g. by exposing the membrane to x-ray film.

The methods employed to prepare the probes of the present invention, and the use of such probes to (a) assign genomic restriction fragments to a given HLA allele, (b) map restriction sites on HLA alleles and (c) determine the HLA type of tissue samples will be further described by reference to the following examples.

Example I—HLA LOCUS SPECIFIC DNA PROBES

A. MATERIALS AND METHODS

1. Cells

The human lymphoblastoid cell line LKT was obtained from the Genetics Laboratory of Oxford University (Oxford, England). The LKT cell line, HLA-A1, -B8, homozygous, was maintained in RPMI-1640 medium (GIBCO) supplemented with 10% fetal calf serum. LCL 721 (HLA-A1, -B8, -A2, -B5) is an Epstein-Barr virus-transformed human B lymphoblastoid cell line. HLA loss mutants were derived from LCL 721 after gamma-irradiation (300 rad; 1 rad=0.01 gray) and selection with complement and alloantisera or monoclonal antibodies against specific HLA antigens.

These gamma-ray induced mutants include LCL 721.45.1, 721.52 and 721.144. See P. Kavathas, et al., PNAS USA, 77, 4251 (1980); H.T. Orr, et al., Nature, 302, 534 (1983), H. T. Orr, et al., Nature, 296, 454 (1982), and R. DeMars et al., Human Immunol., 11, 77 (1984), the disclosures of which are incorporated by reference herein. Mutants 721.45.1 and 721.52 no longer express HLA-A1 or HLA-A2, respectively, due to large deletions of DNA including the HLA-A gene.

Mutant 721.144 has a homozygous deletion of DNA at the HLA-A locus.

Peripheral blood lymphocytes were isolated from a panel of normal donors by the method of A. Boyum, J. Clin. Invest., 21, 77 (1968). HLA class I antigens were typed by the University of Minnesota HLA Typing Laboratory and at the Duke University HLA Typing Laboratory. Table I presents the number of individuals examined expressing each allele and their ethnic origin.

TABLE I

| HLA-A Allele | Number of Individuals | Ethnic Origin |
|---|---|---|
| 1 | 16 | B, $C^{NE}$, O, SA |
| 2 | 11 | B, $C^{NE}$ |
| 3 | 6 | B, $C^{NE}$ |
| 11 | 4 | B, $C^{NE}$, O |
| 23 | 2 | $C^{NE}$ |
| 24 | 4 | $C^{NE}$ |
| 25 | 1 | $C^{NE}$ |
| 26 | 1 | $C^{NE}$ |
| 28 | 2 | $C^{NE}$ |
| 29 | 3 | $C^{NE}$, $C^J$ |
| 31 | 1 | B |
| 32 | 2 | $C^{NE}$ |
| 33 | 2 | B, $C^J$ |
| 34 | 1 | B |
| 36 | 1 | B |

B, Black; $C^{NE}$, Caucasian Northern Europe; $C^J$, Caucasian, Jewish; O, Oriental; SA, Spanish American.

2. Materials

Restriction endonucleases were purchased from Bethesda Research Laboratories, Boehringer Mannheim and New England Biolabs and used according to the supplier's specifications. Nick translation kits and radioisotopes were purchased from Amersham.

3. DNA Isolation and Analysis

Genomic DNA was isolated from lymphoblastoid cell lines and peripheral blood lymphocytes (PBLs) according to Bell, et al. in PNAS USA, 78, 5759 (1981). DNA (10ug) was digested with 20 units of restriction enzyme for 2 hrs at 37° C. and electrophoresed in a 0.7% agarose gel. Prior to blotting, gels were washed in 0.1 M HC1 for 30 mins, then in 0.5 M NaOH plus 1.5 M NaCl for 15 mins and finally in 1 M Tris-HC1, pH 7.5 plus 3.0 M NaCl for 30 mins. The DNA was blotted onto Zetabind (AMF-CUNO) nylon membranes according to Southern, J. Molec. Biol., 98, 503 (1975), the disclosure of which is incorporated by reference herein. After blotting, the membranes were washed briefly in 2x SSC (0.15 M NaCl, 0.01 5 M sodium citrate) and baked in a vacuum oven at 80° C. for 2 hrs.

Prehybridization of the DNA fragments consisted of a 1 hr incubation at 60° C. in 250 ml of 0.1x SSC and 0.1% sodium dodecyl sulfate (SDS) followed by 250 ml of 10x Denhardts medium (Biochem. Biophys. Res. Comm., 23, 641 (1966), 5x SSC, 50 mM Tris-HC1 pH 7.5, 0.1% Na pyrophosphate, 50ug/ml salmon sperm DNA and 1% SDS at 55° C. for 16 hrs.

Hybridization was for 16 hrs at 42° C. in 10 ml of 50% formamide, 5x SSC, 50 mM Tris-HC1 pH 7.5, 0.1% Na pyrophosphate, lug/ml salmon sperm DNA, 10% Dextran sulphate, 1% SDS and $10^6$ cpm/ml of probe which had been nick translated to a specific activity of $10^8$ cpm/ug DNA.

After hybridization with the probes derived from pHLA-1.1 or pHLA-2a.1, the filters were washed initially at 25° C. in 0.15 M NaCl/0.015 M sodium citrate pH7, 0.5% SDS, followed by washing in either 15 mM sodium chloride/1.5 mM sodium citrate, pH 7 at 42° C.

(low stringency) or 15 mM sodium chloride/1.5 mM sodium citrate, pH 7, at 65° C. (high stringency). After hybridization with the probe derived from pHLA-2a.2, the membranes were washed in 2x SSC plus 0.1% SDS at room temperature for 15 mins, 2x SSC plus 0.1% SDS at 60° C. for 30 mins and 0.1x SSC plus 0.1% SDS at 70° C. for 60 min. Hybridizing bands were detected using Kodak XAR film and Dupont lightening Plus screens.

4. Plasmid Starting Materials

HLA-specific c-DNA clone pHLA-1 was prepared by transforming E. coli X1776 with recombinant plasmids prepared by inserting double-stranded (ds) cDNA into the PstI site of pBR322. The ds cDNA was prepared by reverse transcription of HLA m-RNA fractions derived from the LKT cell line. The preparation of a characterization of clone (or plasmid) pHLA-1 is fully described by H. L. Ploegh et al., Proc. Natl. Acad. Sci. USA, 77, 6081 (1980), the disclosure of which is incorporated by reference herein.

The HLA-A2 clone pHLA-2a was prepared by inserting size-selected genomic DNA digests from LCL 721 into the Hind III site of phosphatased pBR322, transfecting bacterial strain LE392 and detecting recombinant bacteria containing class I DNA using pHLA-1 as the probe source. Subsequently, the cloned 5.1 kb fragment containing the HLA-A2 gene was cloned into plasmid pUC9 and designated pHLA-2a. The preparation and characterization of pHLA-2a is fully described by B. Koller et al., in J. Immunology, 134, 2727 (1985), the disclosure of which is incorporated by reference herein. The preparation and a characterization of plasmid pUC9 is fully described by J. Vieira, in Gene, 19, 259 (1982), the disclosure of which is incorporated by reference herein.

The HLA-B7 cDNA clone employed in the hybridization specificity assays was the almost full-length (amino acid 39 to the poly(A)tail) B7 cDNA clone isolated and characterized by A.K. Sood et al., in Proc. Natl. Acad. Sci. USA, 78, 616 (1981).

5. Probes (a) pHLA-2a.1 and HLA.2a.1

The HLA-A locus-specific probe HLA2a.1, was prepared from the genomic clone, pHLA-2a which encodes HLA-A2 from LCL 721. pHLA-2a was digested with restriction endonucleases Pvu II and Msp I. the DNA digest was subjected to electrophoresis in a 5% acrylamide gel. A 490 bp fragment was isolated from the gel according to the procedures of A. Maxam, et al., Methods Enzymol., 65, 499 (1980). The fragment was subcloned into the AccI and SmaI sites of pUC9 to yield pHLA-2a.1 (ATCC No. 53209), and employed to transform E. coil JM 101. By sequence analysis, the subcloned fragment was determined to contain substantially all of the HLA-A2 3' untranslated region and 72bp of 3'-flanking DNA.

(b) pHLA-2a.2 and HLA-2a.2

A second HLA specific DNA probe was constructed according to the procedures of 5(a) from the 180bp HindIII-AluI fragment derived from the 5' end of pHLA-2a to yield pHLA-2a.2 (ATCC No. 53210). Comparison with the sequence analysis of HLA-2A indicates that the subcloned fragment is made up of DNA 5' to the transcriptional unit of the HLA-A2 gene.

FIG. 1 depicts the localization of the subclones pHLA-2a.1 and pHLA-2a.2 used to form the present HLA-A locus specific probes on the genomic clone pHLA-2a.

(c) pHLA-1.1 and HLA-1.1

An HLA-B locus specific probe, HLA-1.1 was prepared by digesting c-DNA clone pHLA-1 with restriction endocnucleases PvuII and PstI. The DNA digest was subjected to electrophoresis in a 5% acryamide gel. A 358 bp fragment was isolated from the gel. This fragment contains only 3'-untranslated sequences of HLA-B8 and does not include the poly(A) tail or poly(A) addition site. The DNA fragment was subcloned into plasmid pUC9 to yield pHLA-1.1 (ATCC No. 53211).

Figure 2:
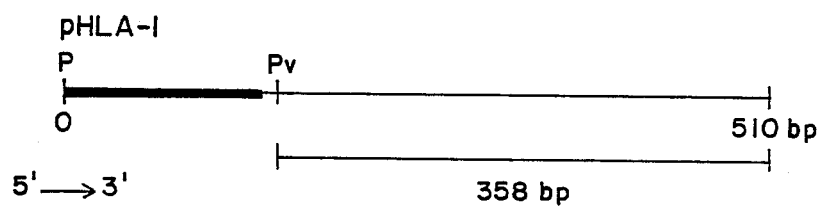
FIG. 2 depicts the localization of the 358bp HLA-B specific probe from the 3'-untranslated region of the HLA-B genomic clone pHLA-1.
Figure 4:
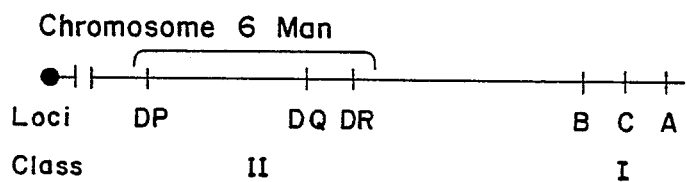
FIG. 4 is a schematic depiction of the location of the loci of the HLA class I and class II genes on chromosome 6.

FIG. 2 depicts the localization of the pHLA-1.1 subclone on pHLA 1. The subcloned DNA fragments were isolated and radiolabelled with $^{32}p$ by nick translation of 0.5 ug of the insert DNA according to the procedure of P. W. Rigby, et al., J. Mol. Biol. 113, 237 (1977).

The labelled DNA fragments were then denatured to form single stranded DNA probes HLA-2a.1, HLA-2a.2 and HLA-1.1 by boiling the fragments for 5 min. in water and quickly chilling them on ice.

B. Hybridization Specificity Assays

1. HLA-A Locus Probe HLA-2a.1

When HLA-2a.1 was used to probe Hind III-digested genomic DNA from LCL 721 at low stringency (15 mM sodium chloride/1.5 mM sodium citrate, pH 7, at 42° C.), a Southern blot pattern very similar to that derived by use of an HLA-B7 cDNA clone was obtained. Only two of the bands visualized with the HLA-B7 cDNA probe failed to hybridize with this HLA-A2 subclone. When the hybridization stringency was increased (15 mM sodium chloride/1.5 mM sodium citrate, pH 7, at 65° C.), a markedly different result was obtained. Although the HLA-B7 cDNA probe continued to hybridize to all but a few of the HindIII-generated fragments at high stringency only two bands continued to bind the HLA-2a.1 probe. One of these, the 5.1-kilobase (kb) fragment has been established to correlate with the expression of the HLA-A2 antigen. The second, a 4.7-kb band has been established to correspond by both an analysis of mutants and population studies to HLA-A1 [see H. T. Orr et al., Immunogenetics, 18, 489–502 (1983)]. To further verify the specificity of the HLA-A probe, DNA was prepared from HLA loss mutants derived from LCL 721. If pHLA-2a.1 is locus specific, hybridization of this probe to these mutant cell lines should correlate with their expression of HLA-A genes. When HindIII-digested DNA from 721.52, an HLA-A2, -B5, -DR1 loss mutant was examined, only the 4.7 kb band seen in the digests from parental cell line 721 was detected. Conversely, when HindIII-digested DNA from the mutant 721.45.1, from which the HLA-A1, -B8, -DR3 haplotype had been deleted was examined the band at 4.7 kb was no longer seen, while the 5.1 kb band remained.

To ensure that the hybridization was HLA-A locus specific, the HLA-A null cell line 721.144 was examined. This line was obtained after gamma-irradiation of the HLA-A1, -B8, -DR3 loss mutant 721.45.1, followed by immunoselection for cells no longer expressing HLA-A2. Both the 4.7, and 5.1 kb fragments were absent from HindIII-digested DNA from line 721.144. Thus, the hybridization data obtained from LCL 721 and the HLA loss mutants show that at high stringency ss DNA from the 3'-untranslated region of HLA-A2 can be used as an HLA-A locus-specific probe.

2. HLA-A Locus Probe HLA-2a.2

Methodology identical to that described for the 3' untranslated region probe, HLA-2a.1, was employed to test the hybridization specificity of HLA-2a.2. Southern blot analysis of LCL 721 and the HLA deletion mutants 721.45.1, 721.52 and 721.144 with the 5' probe HLA-2a.2 under high stringency conditions resulted in patterns identical to those obtained with the 3' probe HLA-2a.1. The HLA-2a.2 probe hybridized to a 5.1 kb and a 4.7 kb fragment generated by the restriction enzyme HindIII in LCL 721. A single band at 5.1 kb was seen in DNA from the HLA-A1:HLA-B8 haplotype deletion mutant 721.45.1. Conversely, in the corresponding HLA-A2:HLA-B5 haplotype deletion mutant 721.52 only the 4.7kb band was detected with HLA-2a.2. No hybridizing bands were seen with HLA-2a.2 in DNA from the HLA-A null deletion mutant 721.144. Thus, the hybridization data obtained from LCL 721 and HLA deletion mutants generated from LCL 721 show that at high stringency ss DNA derived from the 5' flanking region of HLA-A2, HLA-2a.2, is also a HLA-A specific DNA probe.

3. HLA-B Locus Probe HLA-1.1

When HLA-1.1 was used to probe DNA from LCL 721 digested with Bgl II at high stringency, only two bands were seen, one at 7.0 kb and another at 5.8 kb. Examination of haplo-type loss mutants correlated the 7.0 kb band with the HLA-A1, -B8 haplotype and the 5.8-kb band with the HLA-A2, -B5 haplotype--that is, HLA-A, -B8 loss mutants no longer contained a 7.0 kb band while retaining the 5.8 kb band. In HLA-A2, -B5 loss mutants, the 5.8 kb band was no longer detected, while the 7.0 kb band remained.

To determine which locus on the HLA-A1, -B8 haplotype hybridized the probe, Bgl II-digested DNAs from five HLA-B8 loss mutants—721.5, 721.16, 721.10, 721.18, and 721.25—were examined and four were shown to have lost the 7.0 kb band while retaining the 5.8 kb fragment. Mutant 721.16 retained both Bgl II-generated fragments. Earlier hybridization studies using an HLA-B7 cDNA clone as a probe indicated that HLA-B8 single-loss mutants can be divided into two groups, those whose loss of expression of the HLA-B8 gene can be correlated with loss of DNA hybridizing with the HLA-B7 cDNA probe and those in which no loss of class I DNA is apparent. The HLA-B8 loss mutant 721.16 falls into this later category.

As indicated above, the 5.8 kb Bgl II-generated DNA band correlated with the HLA-A2, -B5 haplotype in LCL 721 and therefore was present in the HLA-A1, -B8, -DR3 loss mutant 721.45.1. When mutant 721.45.1 was mutagenized further with gamma-rays to create the HLA-A null line 721.144, the 5.8 kb Bgl II-generated band was retained. As cell line 721.144 has lost the HLA-A2 structural gene, the 5.8 kb fragment that hybridizes with pHLA-1.1 cannot originate from the HLA-A2 gene. Therefore, the 5.8-kb Bgl II-generated DNA fragment contains the HLA-B5 gene or a gene closely associated with it. The strong evidence that pHLA-1 is a clone of the HLA-B8 gene makes it likely that the 5.8 kb band contains the HLA-B5 gene. Therefore, at high stringency the probe obtained from the 3'-untranslated region of an HLA-B cDNA clone, pHLA-1, is an HLA-B specific DNA probe.

4. Hybridization of HLA-2a.1 with HLA-A Alleles (a) HLA-2a.1 was used to probe genomic DNA from unrelated individuals. The Hind III DNA digests from the PBL's of 23 individuals exhibiting 13 HLA-A types were electrophoresed on 0.7% agarose gels. The Southern blots were probed with HLA-2a.1 and washed at high stringency. Two hybridization patterns were observed. In some individuals, two bands were seen. In others, only one band was visualized; however, this band has an intensity double that of a single copy gene. These data, and similar studies with HLA-1.1, indicate that probes from the 3'-untranslated region can generally be used to identify HLA-A and -B genes.

5. Assignment of Restriction Fragments to HLA-A Alleles

To assign HLA-A alleles to DNA restriction fragments detected by the 3' and 5' HLA-A probes, an approach was taken utilizing HLA-A heterozygotes that possessed the HLA-A1 or HLA-A2 allele. Inclusion of DNA from two HLA deletion mutants containing only the HLA-A1 allele, 721.52, which in turn facilitated assignment of those restriction fragments generated from the second HLA-A allel. For example, the hybridization patterns obtained with the 3' probe HLA-2a.1 on SstI digested DNA from a group of 16 individuals having in common the expression of HLA-A1 as summarized on Table I was investigated by Southern blot analysis. In the case of DNA from deletion mutant 721.52, which contains only the HLA-A1 allele, a single band of 3.0 kb hybridized the HLA-2a.1 probe. A hybridizing band of 3.0 kb was also detected in the DNA from all of the HLA-A1 PBLs. Thus the HLA-A1 gene yielded a SstI band of 3.0 kb detectable by the HLA-A 3' specific probe.

DNA from three HLA-A heterozygous individuals also exhibited a single hybridizing band at 3.0 kb. In these cases, it was concluded that the HLA-A allele present in addition to HLA-A1, HLA-A2, -A25 and -A11, also yielded a SstI fragment of 3.0 kb. DNA from three other individuals also yielded a second strongly hybridizing band in addition to the 3.0 kb fragment from HLA-A1. The HLA-A allele other than HLA-A1 was assigned to each additional fragment, i.e. HLA-A32 to the SstI fragment of 8.7 kb and HLA-A3 to a 3.6 kb SstI band.

6. Restriction Site Mapping

In addition to providing the ability to assign HLA-A alleles to segments of genomic DNA, the use of the present HLA-A specific probes in conjunction with the known sequence of the HLA-A2 gene permitted placement of BglII, PvuII, PstI and Sst I recognition sites in DNA flanking the HLA-A2 gene. For example, when 721.52 DNA was digested with SstI, a 3.0 kb fragment was detected with the 3' untranslated probe, HLA-2a.1. The nearest SstI site 5' to the region to which the probe hybridized was identified by comparison with the HLA-A2 DNA sequence, [See B. H. Koller et al., J. Immunol., 134, 2727 (1985) the disclosure of which is incorporated by reference herein]. The 3' end of the SstI fragment detected by the probe was then placed 3.0 kb 3' to the SstI site within the DNA sequence. When digestions of DNA from other HLA-A alleles resulted in fragments identical in size to those of the HLA-A2 gene, the restriction enzyme sites were placed at positions identical to -A2. These placements were confirmed by double digestion with HindIII.

It was of particular interest to map the polymorphic restriction sites. This was accomplished by comparing the size and pattern of the 3' fragments detected after single digestions with BglII, HindIII, PvuII, PstI and SstI with those obtained after double digestions with HindIII and the other four enzymes. Single digestion with HindIII showed that HLA-A1 and HLA-A11 are on 4.7 kb fragments while HLA-A32, -A3, -A2 and -A25 are on 5.1 kb fragments. In addition to fragments derived from HLA-A1, the 3' probe HLA-2a.1 detected polymorphic HindIII-SstI fragments in DNA from HLA-A32, -A3, -A2 and -A25 individuals. Since HLA-A2 and HLA-A25 yielded 3' SstI fragments which did not differ in size from -A1, the -A2 and -A25 polymorphisms detected after HindIII-SstI digestion must be due to the placement of the HindIII site 3' to the HLA-A gene. the 3' HindIII site in -A2 and -A25 maps 400bp 3' of the HindIII site in -A1 or -A11 as depicted on FIG. 3.

Figure 3:
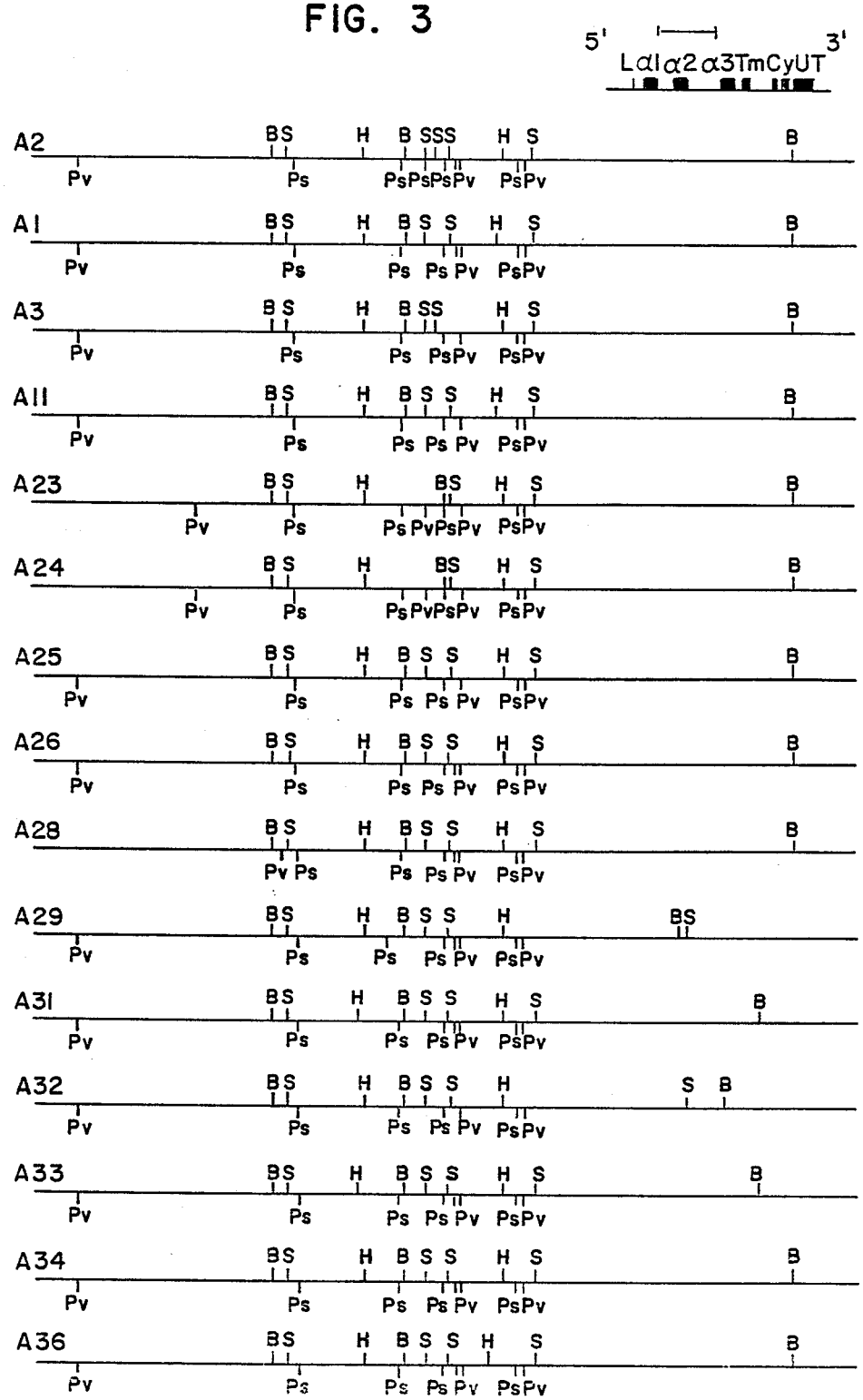
FIG. 3 is a depiction of the placement of restriction enzyme recognition sites within alleles of the HLA-A gene. Corresponding antigenic specificities are indicated to the left of each map. The exon/intron structure of HLA-A2 is indicated above the HLA-A2 map. Between the HindIII sites of HLA-A2 the recognition sites for BgIII, PstI, PvuII and SstI are placed as indicatd by the HLA-A2 DNA sequence. Restriction sites within the other alleles were placed using Southern blotting and the 3' and 5' HLA-A probes of the present invention. Sequences are indicated 5' to 3'. Restriction sites indicated are: B, BgIII; H, HindIII; Ps, PstI; Pv, PvuII; S, SstI.

Since HLA-A32 is also found on a HindIII fragment of 5.1 kb, the 3' HindIII site in -A32 is likely to be located at the same position as in -A2 and -A25. This placement was confirmed by SstI and SstI-HindIII digestions. Since HLA-A32 yielded the same size, 1.9 kb, SstI-HindIII fragment detectable with HLA-2a.1 as HLA-A2 and -A25 did, the 8.7 kb SstI fragment generated from -A32 must be due to the placement of the SstI site 3' to the HindIII site (FIG. 3).

HLA-A3 is another allele associated with a HindIII fragment of 5.1 kb. Thus, the HindIII site 3' to the HLA-A3 gene was placed at a position identical to HLA-A2, -A32 and -A25 (FIG. 3). In HLA-A2 there are two SstI sites in the 3' end of the gene spaced 600 bp apart. The generation of a 3.6kb 3' SstI fragment from HLA-A3 compared to a 3.0 kb SstI fragment from HLA-A2, and the detection of a 2.5 kb SstI-HindIII from HLA-A3 versus a 1.9 kb SstI-HindIII fragment from HLA-A2, placed the SstI site outside of the 3' HindIII site in HLA-A3 at the same place as in HLA-A2 (FIG. 3). therefore, the SstI polymorphism detected by the 3' probe in HLA-A3 is due to an absence of an SstI site 2.5 kb 5' to the 3' HindIII site. This SstI site missing in HLA-A3 was detected in the other 14 alleles and A29 variant examined (FIG. 3).

In an identical manner, the recognition sites were mapped within the 3' end of 15 alleles for the restriction enzymes BglII, PvuII and PstI. Moreover, using an identical strategy and the 5' probe HLA-2a.2 restriction sites for BglII, HIndIII, PvuII, PstI and SstI were mapped within the 5' end of the 15 alleles.

No restriction sites were identified which distinguished the crossreactive group HLA-A2-HLA-A28 from other HLA-A alleles. However, the other crossreactive groups of HLA-A alleles present in this study did contain distinctive restriction sites. The DNA maps for the crossreactive alleles HLA-A23 and HLA-A24 shared two restriction sites not found in the DNA of the other HLA-A alleles studied (FIG. 3), those being the placement of the 3' HindIII site and a BglII site 5' to exon 6. In addition, both HLA-A23 and A-24 lacked 3 restriction sites found in most other HLA-A alleles, a BglII site in exon 3 and SstI sites in exons 4 and 5. Another group of crossreactive alleles studied at the DNA level were HLA-A, -A11 and -A36. These three alleles are the only HLA-A alleles found to be located on a HindIII fragment of 4.7 kb. This fragment size differs from that containing other alleles due to the placement of the 3' HindIII site in -A1, -A11 and -A36. Finally, the crossreactive alleles -A29, -A31, -A32 and -A33 are divided into two subgroups according to restriction map similarities. HLA-A29 and -A32 both have an SstI site located at the same position in their 3' flanking DNA not found in other alleles, lack an SstI site 1.0 kb 3' to the 3' HindIII site found in all other alleles and lack an SstI site in exon 4 found in 11 of the 15 allels studied. HLA-A31 and -A33 have in common two restriction site placements not found in any of the other alleles, i.e. the placement of the HindIII site 5' to the gene and the location of the BglII site in their 3' flanking DNA.

The results summarized in FIG. 3 demonstrate the usefulness of the 5' and 3' locus specific specific probes of the present invention in the analysis of HLA-A alleles at the genomic level. Using the approach presented here, we have mapped restriction sites for 15 alleles of HLA-A. This mapping was done at the genomic level using Southern blotting. The region mapped spans 26 kb of genomic DNA at the HLA-A locus. It should be noted, however, that not all of the BglII, HindIII, PvuII, PstI or SstI sites within the span of DNA depicted in FIG. 5 are mapped. The procedure used maps those recognition sites most proximal to the two probes HLA-2a.1 (3') and HLA-2a.2 (5').

Placement of restriction sites within the HLA-A3 and HLA-A24 alleles was verified upon analysis of DNA sequences available for these two alleles as reported, for example, by T. Strachen, et al., EMBO J., 3, 887 (1984). this provides a confirmation of the method described here for restriction mapping HLS alleles. Moreover, this verification provides further evidence that both HLA-2a.1 and HLA-2a.2 are HLA-A specific DNA probes.

Although only 5 restriction enzymes were used in this study, it was possible to detect polymorphic fragments unique to four HLA-A alleles. These fragments resulted from the following polymorphic sites: a PvuII site within the 5' flanking DNA of HLA-A28, BglII sites within the 3' flanking DNA of HLA-A29 and HLA-A32, a PstI site in exon 2 of HLA-A29 and an absence of a SstI site in the 3' region of the HLA-A3 gene. This latter SstI site was found in the 3' region of the remaining 14 HLA-A alleles examined. It is expected that a more exhaustive study using the approach described in this report should detect more allelespecific polymorphic restriction fragments.

An important aspect of this search is the identification of those polymorphic sites which map within the respective HLA genes. Polymorphic sites within the HLA genes are the most useful for HLA typing since such sites will not be separated from the HLA gene by recombination. Recombination could result in a false assignement of an HLA allele when the assignment is based on the identification of a polymorphic site mapping to DNA flanking an HLA gene.

7. Tissue Typing with DNA Probes

To use DNA probes to determine an individual's HLA type, a 15 ml sample of blood would first have to be obtained. From this sample genomic DNA (about 150 mg) would be prepared as described hereinabove. This DNA would then be divided into three aliquots to be assayed for the HLA-A, HLA-B and HLA-C genes. Each aliquot would then be subdivided into 10 samples for digestion with 10 different restriction endonucleases. The number of restriction endonucleases needed is an estimate of the number required to ensure that each allele can be unambiguously identified. After digestion, each group of 10 samples will then be run on separate agarose gels and blotted onto a nylon membrane to generate three membranes for each individual being typed. One membrane would then be probed with an HLA-A probe, the second with an HLA-B probe and the third with an HLA-C probe. Since nylon membranes are used, each membrane could be stripped and reprobed with the other gene specific probes for HLA- A, HLA-B and/or HLA-C. The resulting hybridization bands would then be compared to a database of allele specific bands. This database would be generated in the manner described hereinabove and depicted graphically in FIG. 3. Analysis would be most efficiently handled by a microcomputer and appropriate software. If fluorescently labeled probes were being used, only one gel would have to be run since hybridization of the HLA-A, -B and -C probes could be distinguished by their spectral emissions. Consequently, this would reduce the amount of tissue, i.e. blood, needed by two thirds.

In summary, the present HLA-A locus specific probes have provided a rapid and straightforward method for the placement of restriction endonuclease sites within the alleles of class I loci such as HLA-A. In turn, the allele-specific fragments can be employed to HLA-type human tissue. The use of these probes in conjunction with the HLA-B specific probe of the present invention and with other class I loci probes prepared by the present method should substantially assist in the molecular genetic characterization of the polymorphism of the entire human class I gene family. In a similar manner class II loci-specific probes such as those derived from HLA-DR, HLA-DQ and HLA-DP genes could be employed to characterize the HLA class II gene family.

As indicated hereinabove, *E. coli* LE 392 strains carrying plasmids pHLA-2a.1, pHLA-2a.2 and pHLA-1.1 have been deposited with the American Type Culture Collection (ATCC), Rockville, Md. and their assigned accession numbers are given.

A culture of the deposited microorganisms will be made available to the public upon the grant of patent based upon the present application. It is to be understood that the availability of a deposit does not constitute a license to practice the subject invention in derogation of patent rights granted by the United States government. Furthermore, the present invention is not to be limited in scope by the microorganism deposited, since the deposited embodiment is intended as a single illustration of one aspect of the invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A DNA probe comprising a single strand of detectably labeled DNA which hybridizes specifically with single-stranded DNA derived from substantially all of the alleles present at only one HLA class I locus, and wherein said labelled DNA is derived from the 3'-untranslated region or from the 5'-flanking region of one of said alleles of said class I locus.

2. The probe of claim 1 wherein said HLA class I locus is an HLA-A locus, an HLA-B locus or an HLA-C locus.

3. the probe of claim 2 wherein said class I locus allele is the HLA-A2 gene.

4. The probe of claim 3 wherein said HLA-A2 gene is derived from a human lymphoblastoid cell line.

5. The probe of claim 4 wherein said lymphoblastoid cell line is LCL-721 or a deletion mutant thereof.

6. The probe of claim 3 which comprises substantially all of the 3'-untranslated region of the HLA-A2 gene.

7. The probe of claim 6 which comprises the denatured, labelled 490 basic pair Pvu II - Msp I fragment of plasmid pHLA-2a.

8. The probe of claim 7 which is prepared by a process comprising cloning the 490 base pair Pvu II - Msp I fragment from plasmid pHLA-2a into the Acc I and Sma I sites of plasmid pUC9 to yield plasmid pHLA-2a.1.

9. The probe of claim 3 which comprises DNA 5' to the transcription region of the HLA-A2 gene.

10. The probe of claim 9 which comprises the denatured, labelled 180 base pair Hind III - Alu I fragment of plasmid pHLA-2a.

11. The probe of claim 10 which is prepared by a process comprising cloning the 180 base pair Hind III - Alu I fragment of pHLA-2a into the Acc I and Sma I sites of plasmid pUC9 to yield plasmid pHLA-2a.2.

12. The probe of claim 2 wherein said HLA class I locus allele is the HLA-B8 gene.

13. The probe of claim 12 wherein said HLA-B8 gene is derived from a human lymphoblastoid cell line.

14. The probe of claim 13 wherein the lymphoblastoid cell line is LKT (HLA-A1, -B8, homozygous).

15. The probe of claim 12 which consists essentially of a DNA sequence from the 3'-untranslated region of the HLA-B8 gene.

16. The probe of claim 15 which comprises the denatured, labelled 358 base pair Pvu II - Pst I fragment of plasmid pHLA-1.

17. the probe of claim 16 which is prepared by a process comprising cloning the 358 base pair Pvu II - Pst I fragment of pHLA-1 into the Acc I and Sma I sites of plasmid pUC 9 to yield plasmid pHLA-1.1.

18. A method for identifying DNA derived from an HLA-A gene comprising denaturing said DNA and hybridizing said denatured genomic DNA with the probe of claim 6 or claim 9 and detecting the denatured genomic DNA fragments which have hybridized with said probe.

19. A method for identifying DNA derived from HLA-B gene comprising denaturing said DNA and hybridizing said denatured DNA with the probe of claim 15, and detecting the denatured genomic DNA fragments which have hybridized with said probe.

* * * * *